US012678068B2

(12) United States Patent 
Andrasko et al.

(10) Patent No.: US 12,678,068 B2 
(45) Date of Patent: Jul. 14, 2026

(54) SYSTEM AND METHOD FOR BREATH SAMPLING AND BREATH ANALYSIS

(71) Applicant: Pinsalus AB, Ullared (SE)

(72) Inventors: Jan Andrasko, Vreta Kloster (SE); Ludmila Lagesson-Andrasko, Linköping (SE); Thomas Lundeberg, Lidingö (SE)

(73) Assignee: PINSALUS AB, Ullared (SE)

( * ) Notice: Subject to any disclaimer, the term of this patent is extended or adjusted under 35 U.S.C. 154(b) by 335 days.

(21) Appl. No.: 18/286,050

(22) PCT Filed: Apr. 8, 2022

(86) PCT No.: PCT/SE2022/050357 
§ 371 (c)(1), 
(2) Date: Oct. 6, 2023

(87) PCT Pub. No.: WO2022/216217 
PCT Pub. Date: Oct. 13, 2022

(65) Prior Publication Data 
US 2024/0197202 A1 Jun. 20, 2024

(30) Foreign Application Priority Data 
Apr. 8, 2021 (SE) ..................................... 2150438-6

(51) Int. Cl. 
*A61B 5/08* (2006.01) 
*A61B 5/00* (2006.01) 
(Continued)

(52) U.S. Cl. 
CPC .............. *A61B 5/082* (2013.01); *A61B 5/097* (2013.01); *A61B 5/6803* (2013.01); *G01N 33/497* (2013.01)

(58) Field of Classification Search 
CPC ....... A61B 5/082; A61B 5/097; G01N 33/497 
See application file for complete search history.

(56) References Cited

U.S. PATENT DOCUMENTS 5,081,871 A 1/1992 Glaser 
5,284,054 A * 2/1994 Loebach .............. G01N 33/497 
73/23.3 
(Continued)

FOREIGN PATENT DOCUMENTS

EP 1726258 A2 11/2006 
WO 99/20177 A1 4/1999 
(Continued)

OTHER PUBLICATIONS

International Preliminary Report on Patentability received for PCT Patent Application No. PCT/SE2022/050357, mailed on Jun. 2, 2023, 8 pages. 
(Continued)

*Primary Examiner* — Daniel L Cerioni 
(74) *Attorney, Agent, or Firm* — MEDLER FERRO WOODHOUSE & MILLS PLLC

(57) ABSTRACT

A system for breath analysis includes a breath sampling apparatus for collecting substances from the exhalation breath of a test subject; and a sample preparation apparatus for extracting selected analytes. The method includes: placing a sampling disc in the proximity of exhalation openings of a test person; receiving exhalation breath on the sampling disc for a predetermined period of for example about 1 hour; collecting a sample of substances from the exhalation breath by adsorption on the sampling disc corresponding to the average amount and composition of substances exhaled during a length of time; placing the sampling disc with the collected substances in a desorption vessel; releasing the collected substances from the sampling disc in the desorption vessel by heating in an inert atmosphere; preparing the sample by adsorption of selected analytes among the sample of substances; and analyzing selected analytes by gas chromatography.

17 Claims, 6 Drawing Sheets

100

102

108

104

106

(51) Int. Cl.
    *A61B 5/097*        (2006.01)
    *G01N 33/497*     (2006.01)

(56)           References Cited

U.S. PATENT DOCUMENTS

| | | | |
|---|---|---|---|
| 5,479,815 | A | 1/1996 | White et al. |
| 8,932,525 | B1 | 1/2015 | Ahmad et al. |
| 9,357,946 | B2 | 6/2016 | Johnson et al. |
| 2005/0065446 | A1* | 3/2005 | Talton .................... A61B 5/097 |
| | | | 73/23.3 |
| 2006/0266353 | A1 | 11/2006 | Yamada et al. |
| 2008/0092629 | A1 | 4/2008 | Suga et al. |
| 2018/0242884 | A1 | 8/2018 | Kulkarni et al. |
| 2019/0203256 | A1 | 7/2019 | Koo et al. |
| 2019/0350495 | A1* | 11/2019 | Ahmad .................. A61B 5/097 |
| 2021/0212597 | A1* | 7/2021 | Allsworth .............. A61B 5/097 |

FOREIGN PATENT DOCUMENTS

| | | | |
|---|---|---|---|
| WO | 2005/010482 | A2 | 2/2005 |
| WO | 2016/092280 | A1 | 6/2016 |
| WO | 2018013946 | A1 | 1/2018 |
| WO | 2019/066633 | A1 | 4/2019 |

OTHER PUBLICATIONS

International Search Report and Written Opinion received for PCT Patent Application No. PCT/SE2022/050357, mailed on Jun. 20, 2022, 17 pages.

* cited by examiner

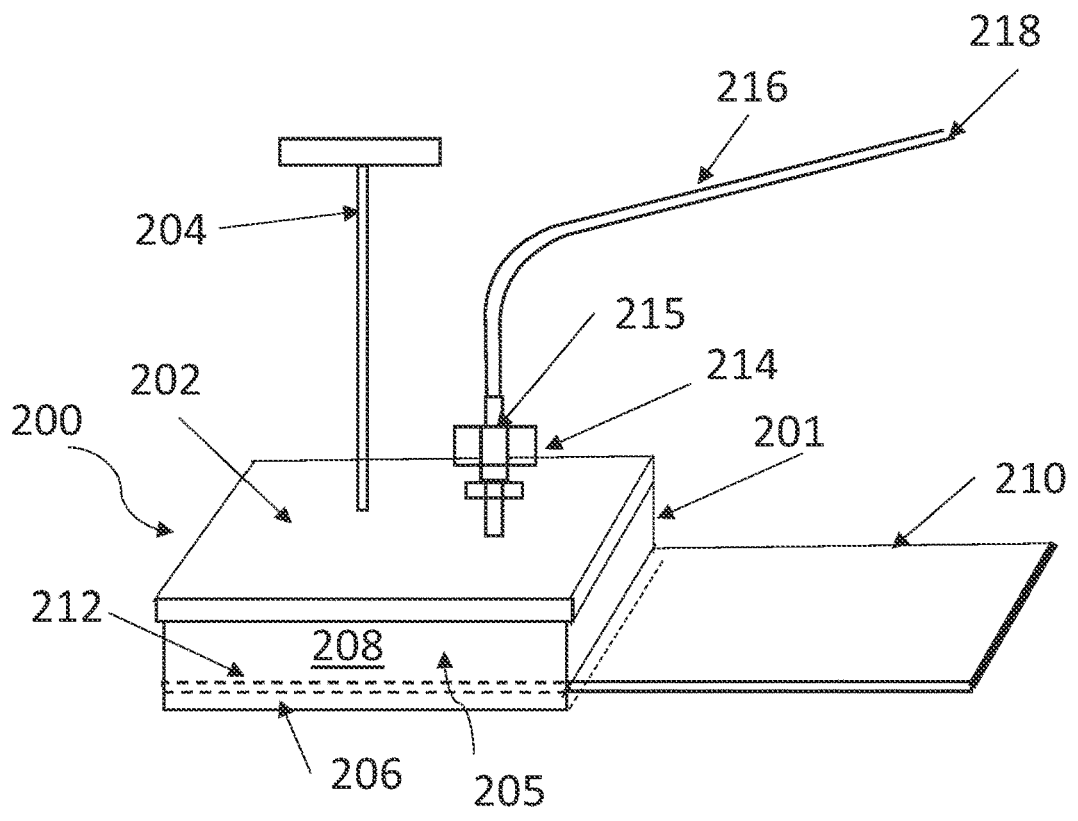
FIG 2A
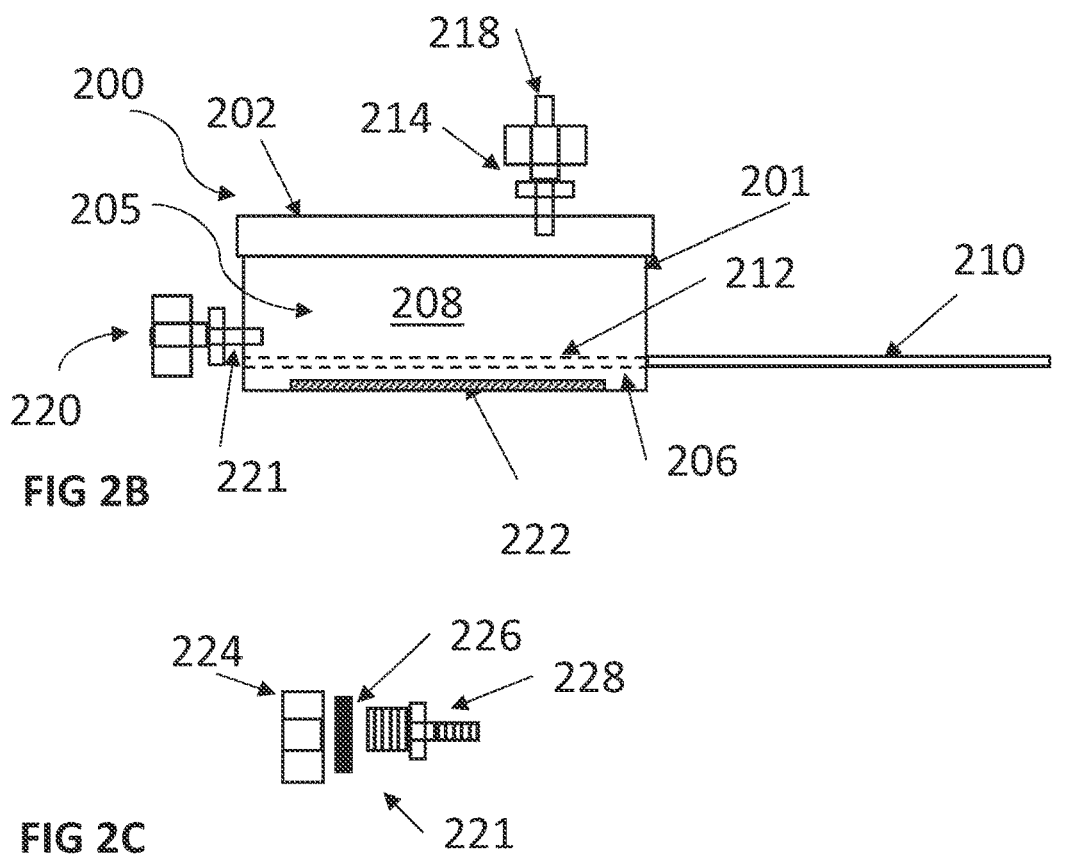
FIG 2B
FIG 2C

Phase 1

Phase 2

Phase 3A

Phase 3B

Phase 1

Phase 3A

Phase 3B

SYSTEM AND METHOD FOR BREATH SAMPLING AND BREATH ANALYSIS

CROSS-REFERENCE TO PRIOR APPLICATIONS

This application is a § 371 National Stage Application of PCT International Application No. PCT/SE2022/050357 filed Apr. 8, 2022, which claims the priority of Swedish Application No. 2150438-6, filed Apr. 8, 2021, each of which are herein incorporated by reference in their entirety.

TECHNICAL FIELD

The present disclosure pertains in general to apparatus and methods for breath sampling and breath analysis.

BACKGROUND

Breath exhaled from a living being contains various substances that can be indicative of different kinds of health status, conditions or diseases. Substances in the form of volatile organic compounds in breath gas are collected and analyzed to detect presence and to measure levels of substances that represent biomarkers for different pathologies such as cancer or different lung diseases. The concentration of such substances in breath is in general very low and sampling need be performed with different techniques to produce reliable results.

There is in related art a variety of methods for analyzing breath and for detecting substances present in samples of breath.

RELATED ART

Examples of related art are found in the following publications.

The patent publication U.S. Pat. No. 9,357,946 B2 shows a direct sampler and detector for analytes found in exhaled breath condensate. In this publication, analytes in breath condensate are detected instantaneously as they condense prior to reaching the sensor surface or condense directly on the sensor surface.

Object of the Present Disclosure

The general object of the present disclosure is to provide a system, system components and a method for breath sampling and breath analysis that renders a reliable detection and measure of selected substances present in exhalation breath.

More specifically, further objects of the present disclosure include providing solutions to partial problems, such as:
collecting a sample of substances from exhaled breath;
extracting analytes from a sample of substances;
analyzing analytes extracted from a sample of substances.

SUMMARY

The mentioned objects are addressed by embodiments described herein, where a system for breath analysis, comprises a breath sampling apparatus configured for collecting, from the exhalation breath of a test subject, a sample of substances on a sampling disc devised with an adsorbent; and a sample preparation apparatus configured for extracting selected analytes from a sample of substances collected on said sampling disc.

Embodiments further comprises one or more of the following aspects, inter alia a system or a device:
wherein the breath sampling apparatus comprises a headset (102) having a holder (104) for a sampling disc (106) prepared with an adsorbent;
wherein the holder (104) being arranged on the headset (102) such that the holder (104) is adjustable to be placed in the proximity of exhalation openings of a test person when carrying the headset;
wherein the breath sampling apparatus is devised such that a sampling disc (106) is attachable by means of a magnet or other mechanical arrangement.

Embodiments further comprises one or more of the following aspects, inter alia a system or a device:
wherein the breath sampling apparatus (600) comprises a mouthpiece (602) coupled for fluid communication of exhalation breath to a sampling vessel (604) adapted for housing a said sampling disc (106);
wherein the breath sampling apparatus further comprises a valve mechanism (108) adapted for venting off an amount of exhalation breath to reduce the amount of dead space air entering the sampling vessel (604);
wherein the breath sampling apparatus (600) is configured to cool the exhalation breath before, during or after the exhalation breath has been collected in the sampling vessel in order to condense any water vapor from the exhalation breath to reduce water content on the sampling disc (106) and/or in the atmosphere in the sampling vessel.

Embodiments further comprises one or more of the following aspects, inter alia a system or a device:
further comprising a sampling disc (106) having a disc member, for example of metal, provided with an adsorbent attached to a surface area of the disc member;
wherein the sampling disc (106) comprises an adsorbent powder glued to the disc member.

Embodiments further comprises one or more of the following aspects, inter alia a system or a device:
wherein the sample preparation apparatus comprises a desorption vessel (200) having a main casing (201) and a top lid (202), the desorption vessel adapted to accommodate a said sampling disc and further being provided with an inlet port (214) for inlet of an inert gas and an outlet port (220,250) for outlet of desorbed substances from the interior of the desorption vessel;
wherein the desorption vessel (220) comprises a slidable lid (210) adapted to selectively partition the interior of the desorption vessel into two chambers when fully inserted, such that a first chamber (206), preferably having a small volume, is formed in the desorption vessel to be able to accommodate a sampling disc, and a second chamber (208), preferably having a larger volume; such that said second chamber (208) is fully exposed to a sampling disc placed in the first chamber (206) when the slidable lid (210) is extracted and that said second chamber is substantially unaffected by a sampling disc placed in the first chamber (206) when the slidable lid (210) is fully inserted;
wherein the sample preparation apparatus comprises a moisture trap (256,258) adapted to condense and possibly freeze any water content present with the desorbed substances extracted from the desorption vessel (220).

Embodiments further comprises one or more of the following aspects, inter alia a system or a device:

comprising a breath sample container for intermediate storage of a sampling disc with a sample of substances collected from the exhalation breath of a test subject;

comprising an apparatus for detecting and measuring analytes in a collection of substances extracted from a sampling disc, for example in the form of apparatus for Gas chromatography-vacuum ultraviolet spectroscopy GC-VUV, mass spectrometry MS, flame ionization detection FID or some other suitable detection and/or measurement apparatus.

Embodiments of a method of breath analysis comprises: placing a sampling disc devised with an adsorbent in the proximity of exhalation openings of a test person; receiving exhalation breath on the sampling disc for a predetermined period of for example about 1 hour; collecting a sample of substances from the exhalation breath by adsorption on the sampling disc, wherein the adsorbed amount and composition of substances corresponds to the average amount and composition of substances exhaled during a length of time; placing the sampling disc with the collected substances in a desorption vessel; releasing the collected substances from the sampling disc in the desorption vessel by heating in an inert atmosphere; preparing the sample by adsorption of selected analytes among the sample of substances; analyzing said selected analytes by means of gas chromatography.

Method embodiments further comprises one or more of the following aspects, inter alia a method:

further comprising capturing any water content present among the collected substances by condensation, for example by means of a moisture trap;

wherein preparing the sample further comprises adsorption of said selected analytes by means of Solid Phase Microextraction (SPME);

wherein preparing the sample further comprises adsorption of said selected analytes by means of a Needle Trap Device (NTD);

wherein analyzing said selected analytes comprises analysis by means of a selection of: Gas chromatography-vacuum ultraviolet spectroscopy GC-VUV, mass spectrometry MS, flame ionization detection FID or some other suitable detection method.

BRIEF DESCRIPTION OF THE DRAWINGS

The technology of the present disclosure will be further explained below with reference to the accompanying drawings, wherein:

FIG. 2A-FIG. 2C shows an exemplifying embodiment of a sample preparation apparatus configured for extracting selected analytes from a collected sample of substances.

DETAILED DESCRIPTION

Figure 1A:
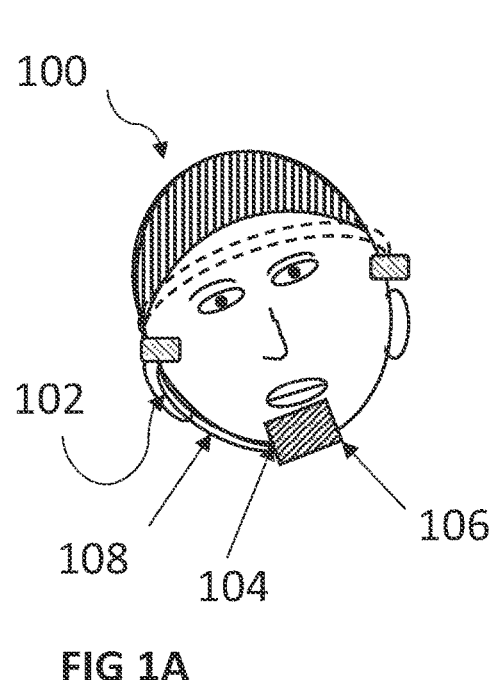
FIG. 1A-1D show exemplifying embodiments of a breath sampling system comprising an embodiment of a breath sampling apparatus in the shape of a headset configured for collecting a sample of substances from the exhalation breath of a test subject.
Figure 1B:
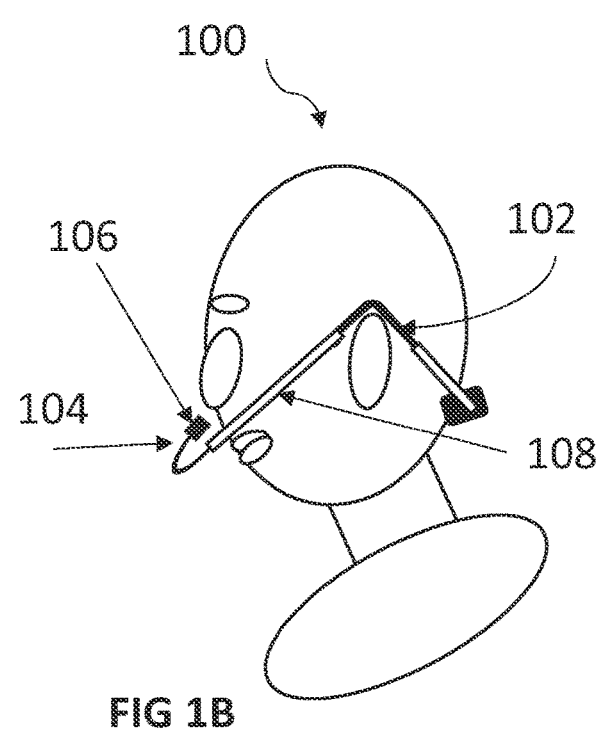
Figure 1C:
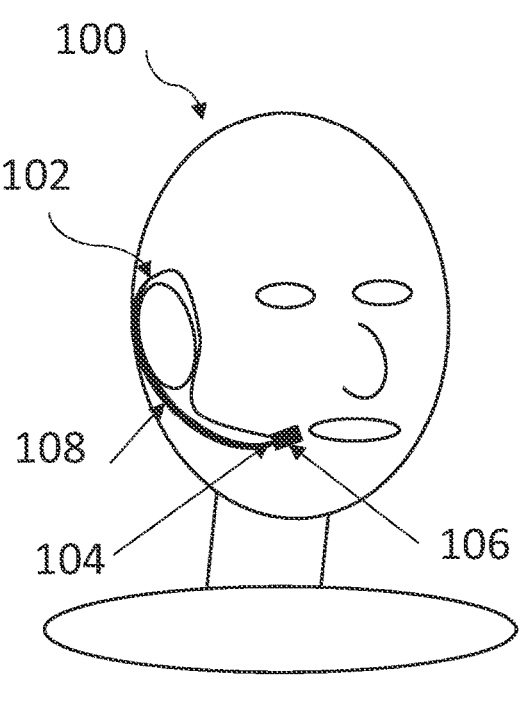
Figure 1D:
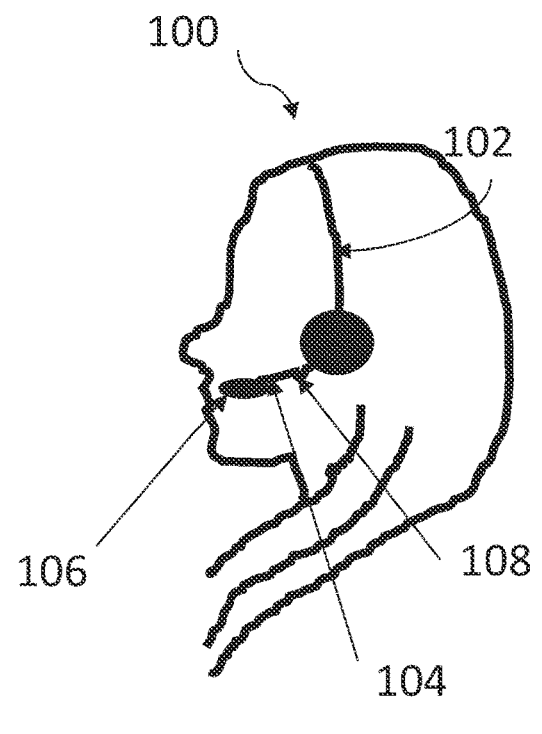

Breath exhaled from a living being among air breathing animals contains substances that can be indicative of health status, conditions and diseases. Detection and measuring of such substances can be used to obtain diagnostic information and other information, herein in short called status information. Exemplifying embodiments are shown and described herein mainly with reference to human test subjects, whereas the invention as a whole pertains to and is applicable on other air breathing animals with appropriate adaptations.

In order to obtain such status information of good quality or for certain purposes it is important to collect substances from the exhaled breath of a test subject over a certain period of time.

Sampling Apparatus and Sampling Disc

FIG. 1A-1D show exemplifying embodiments of a breath sampling apparatus comprising a headset configured for collecting a sample of substances from the exhalation breath of a human being as a test subject. In these embodiments, a headset is provided with a holder for a sampling disc prepared with an adsorbent. FIG. 1A to 1D show different examples of such headsets 102 applied to the head or to the ears of an individual test person 100 giving the breath sample. A holder 104 for a sampling disc 106 is mounted on a boom 108 in similarity with the way a microphone would be mounted on a telephone or on a speaker headset. In embodiments the sampling disc 106 may be attached to the boom by means of a magnet or other mechanical attachment arrangement (not shown). In use, i.e. when sampling breath and collecting a sample of substances contained in the breath, the boom 108 shall be adjusted such that the sampling disc is placed in the proximity of exhalation openings, i.e. in front of the mouth and/or of the nose of a test person e.g. in the area between the mouth and the nose.

Figure 6:
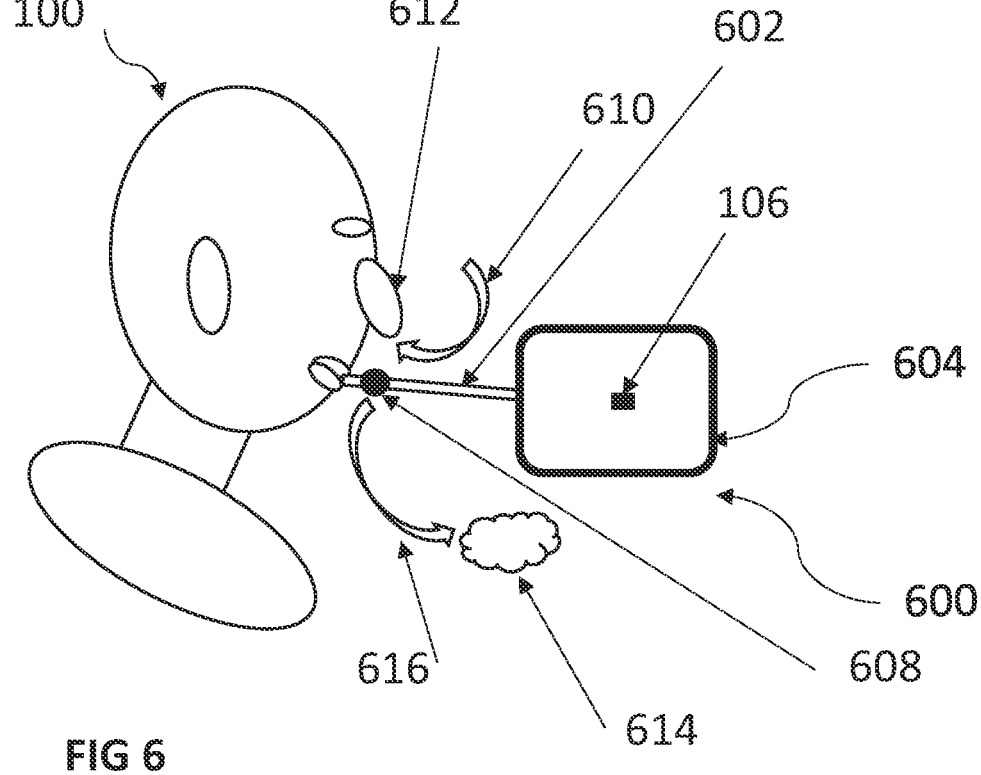
FIG. 6 illustrates schematically a further embodiment of a breath sampling apparatus adapted to eliminate dead space air affecting a sample.

FIG. 6 shows another embodiment of a breath sampling apparatus 600 that comprises a mouthpiece 602 coupled for fluid communication of exhalation breath to a sampling vessel 604 adapted for housing a sampling disc 106 devised with an adsorbent. The sampling vessel 604 is in embodiments in the shape of a gas sampling bag adapted to accommodate such a sampling disc and in other embodiments a hard structure. The gas sampling bag may be a Tedlar bag or a similar structure. An advantage with a sampling vessel formed in a soft structure like a bag is that the sampling vessel may be substantially empty of any atmosphere in an inflated state, or possibly primed with an inert gas such as nitrogen, and expand when filled with exhalation breath from the test subject. In other embodiments the sampling vessel may be formed by a hard structure and should in such a case be devised such that no atmosphere can affect any exhalation breath collected therein. The sampling vessel is preferably provided with a check valve to prevent collected exhalation breath to escape.

As illustrated in FIG. 6, when sampling the test subject 100 inhales ambient air through the nose 612 and exhales breath into sampling vessel 604 via the mouthpiece 602. The arched arrow 610 illustrates the general direction of the ambient air flow. In the sampling vessel, the sampling disc is mounted such that it is exposed to breath and adsorbs substances from the breath.

Embodiments of this breath sampling apparatus 600 further comprises a valve mechanism 608 adapted for venting off an amount of exhalation breath 614 to reduce the amount of dead space air entering the sampling vessel 604. The arched arrow 616 illustrates the general direction of the vented off exhalation breath 614. The dead space is the term for a volume of air that is not subject to gas exchange in the lungs of a test person. The dead space exhalation breath is thus of little or no value for the sampling purpose since it would not contain any or very little of substances that are targeted for collecting on the sampling disc. By venting off the dead space exhalation breath the sampling vessel un-necessary filling of the sampling vessel and dilution of the collected exhalation breath is avoided. In embodiments, the valve mechanism is devised such that in each exhalation or breath cycle it vents off a certain preset or pre-settable volume of exhalation breath and then switches to conduct the remaining exhalation breath into the sampling vessel.

Further embodiments of this breath sampling apparatus 600 is configured to cool the exhalation breath before, during or after the exhalation breath has been collected in the sampling vessel 604 in order to condense any water vapor from the exhalation breath to reduce water content on the sampling disc (106) and/or in the atmosphere in the sampling vessel. Fore example, this may in embodiments be realized by a moisture trap comprising a cooling element in the flow path of the exhalation breath, for example coupled to or integrated with the mouth piece or the sampling vessel.

Sampling Disc

In embodiments the sampling disc 106 comprises a disc member, for example made of metal or a metal alloy such as steel in sheet metal. A normal size of the disc member would e.g. be in the range of 30×40 millimeters (mm) when it is designed with a rectangular shape, in the range of 1 milli-meter (mm) thick and with an approximate surface area in the range of 1 200 square millimeters. In embodiments, the disc member may be designed with other shapes such as square, round, circular or oval with a similarly sized thick-ness and surface area.

The disc member is prepared with an adsorbent. In embodiments, a glue such as a black silicon glue e.g. Casco® Silikon 300° C. is spread on one or both surface areas of the disc member, and an adsorbent powder is pushed into the sticky glue surface. The adsorbent powder shall stick to the glue and form an even layer of adsorbent on the whole of or substantially the whole of the glue provided surface area. Surplus adsorbent powder that does not stick to the glue is removed for example by carefully blowing it away. When preparing the disc member, the silicon glue stiffens or hardens after about 20 minutes.

For adsorbent, embodiments comprise a hydrophobic adsorbent such as Poropak Q®, Tenax TA® or Carbopack X® with suitable particle size in the range of about 80-100 mesh. With this configuration, no water vapor will stick to the adsorbent or to the glue. The selection of adsorbent depends on different requirements, purposes or targets of the breath sampling. For example, the adsorbent Tenax TA® is more suitable for less volatile substances, and less suitable or even directly unsuitable for very volatile substances since the latter are adsorbed to a smaller extent. Carbopack X® is for example suitable for very volatile substances, whereas less volatile substances stick too firmly to this adsorbent and are hard to desorb in a satisfying quantity. Porapak Q® is for example suitable for volatile as well as for less volatile substances, but it does not withstand high desorption tem-peratures and will thus require a moderate desorption tem-perature. In embodiments, a mixture of one or more adsor-bents with different properties and qualities, for example the adsorbents mentioned above, is advantageously used.

Before use in sampling breath gas, the sampling disc with the glue and the adsorbent must be conditioned. In embodi-ments conditioning of the sampling disc is made by heat treatment in an oven. The temperature and the time of the conditioning heat treatment is different dependent on the selected adsorbent. For example, for the adsorbent Carbo-pack X® conditioning comprises heat treatment with 300° C. (degrees Celcius) for 2 hours. The conditioning must be performed in an inert atmosphere, for example in a nitrogen atmosphere, possibly using a gas chromatograph to check and/or control the contents of the conditioning atmosphere.

In embodiments of the conditioning procedure, the sam-pling disc is enclosed, e.g. in a pouch such as an aluminum pouch, and is heated to a selected conditioning temperature under a constant flow of an inert gas such as nitrogen gas. The conditioning may be performed in a desorption vessel.

After conditioning, the sampling disc is stored in a tightly closed enclosure, for example a box, a metal box, a bag or a pouch.

Sampling Procedure

As described above, a test person 100 carries a headset 102 of a sampling apparatus with a conditioned sampling disc 106 positioned in the vicinity of the exhalation open-ings.

In a sampling protocol of the present disclosure, the test person shall breath in a normal manner such that the sampling disc 106 is exposed to exhalation gas, i.e. exhaled breath gas, and consequently also to inhalation of ambient air for a period in the range of 1 hour.

In the sampling phase, substances in the exhalation gas are collected on the sampling disc 106 by adsorption. By sampling in this manner, the adsorbed amount and compo-sition of substances will correspond to an average of what is exhaled during a length of time. After sampling, possible residual water vapor is removed from the sampling disc by blowing an inert gas such as nitrogen gas over the sampling disc e.g. during a period in the range of 1 minute at room temperature.

After the sampling has been conducted for a preferably prescribed time, e.g. for about 1 hour as mentioned above and possibly residual water vapor has been removed, the sampling disc may be put in a sample storage box for transport to an analysis facility or for storage awaiting analysis. In such a case the sampling may be performed in the home of a patient and the sample storage box can be stored in cool temperature preferably in a refrigerator and/or be sent to an analysis facility for analysis.

The sampling disc may also be directly placed in a desorption vessel of a sample preparation apparatus in cases when an analysis is performed in conjunction with the sampling procedure.

Desorption

In preparation for analysis the sampled substances need be released from the sampling disc. This is done in a desorption procedure using a sample preparation apparatus.

First Embodiment of Desorption Vessel and Desorption Method

FIG. 2A-2C shows an exemplifying embodiment of a sample preparation apparatus configured for extracting selected analytes from a collected sample of substances.

Embodiments of the sample preparation apparatus com-prises a desorption vessel 200, for example designed as a quadrangular box, having a main casing 201, a top lid 202 and a handle 204 for lifting the desorption vessel 200 and/or for lifting the lid 202 of the desorption vessel. The material of the desorption vessel may for example be steel or other suitable metal or metal alloy.

Figure 3:
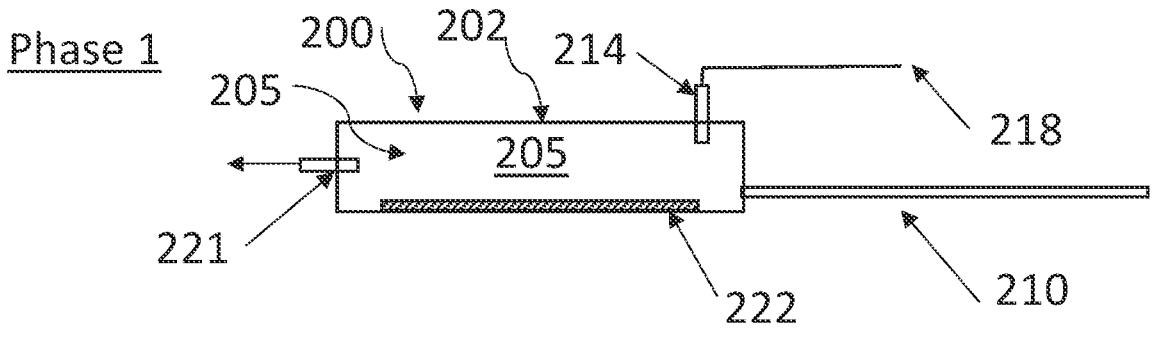
FIG. 3 illustrates schematically a first method for extracting selected analytes from a collected sample of substances with a sample preparation apparatus according for example to the embodiment of FIG. 2.
Figure 3:
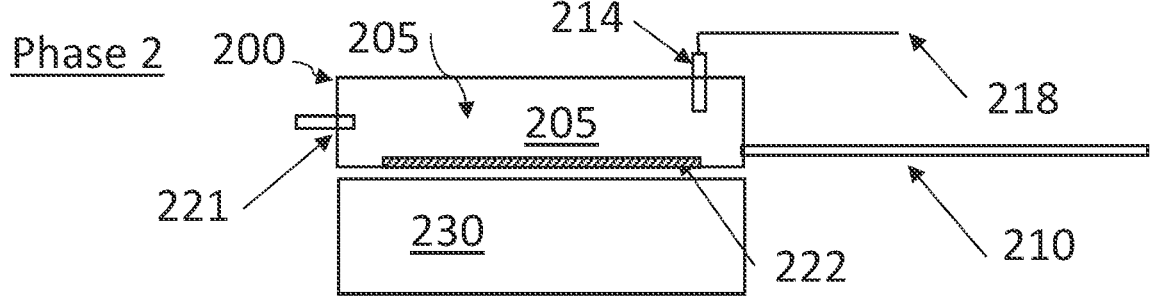
Figure 3:
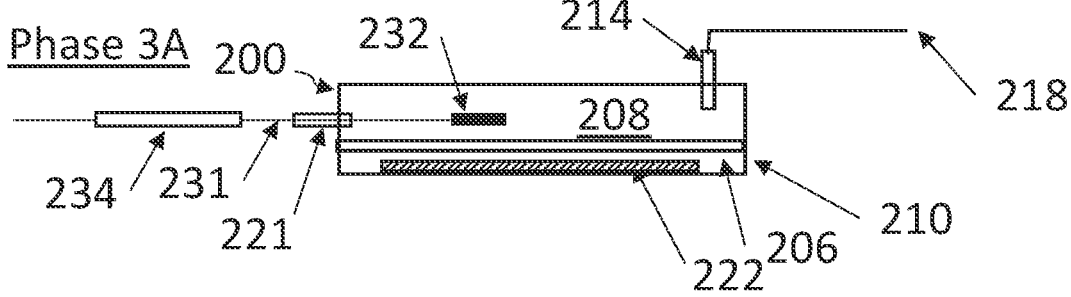
Figure 3:
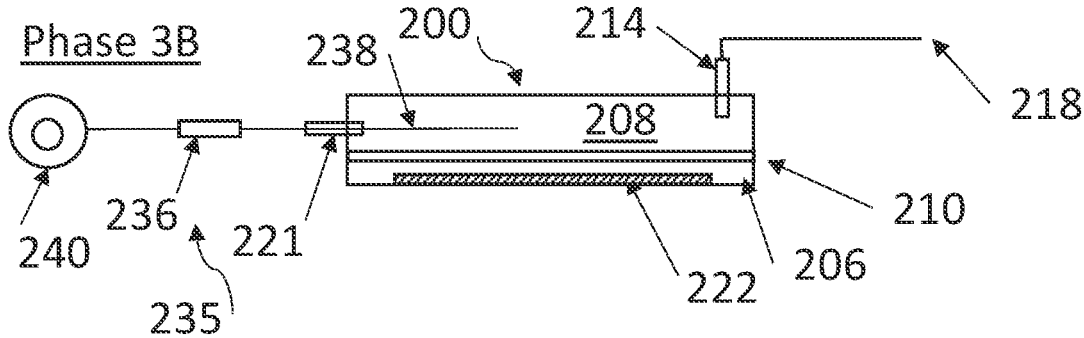

The desorption vessel 200 has a tightly fitting and sealing top lid 202 and an interior chamber 205 that is divisible by means of a slidable lid 210 into a first smaller volume sampling disc chamber 206 at the bottom part of the box and a larger volume desorption chamber 208 at the upper part of the box, as is also shown in Phase 3A and Phase 3B parts of FIG. 3. The sampling disc chamber 206 should be adapted to house a sampling disc 222 with its adsorbent material with as small volume as possible. When the slidable lid 210 is fully slid into the box through a slot in on one of the side walls and guided by guiding grooves 212 at the interior walls of the box, the two chambers 206 and 208 should be tightly separated, preferably wholly or substantially sealed, from each other. This entails that the atmosphere in the interior chamber 205 is divided into a small part in the smaller volume chamber 206 that fills the space around the adsorbent and into a larger part in the larger volume chamber 208 that fills a space that is unaffected or substantially unaffected by the adsorbent when the slidable lid 210 is closed. When the slidable lid 210 is extracted to its maximum as shown in FIG. 2A, the sampling disc with the adsorbent is fully exposed in the interior chamber, i.e. not shielded by the slidable lid, and the slidable lid blocks and substantially seals the slot from the ambient atmosphere.

The height from the bottom of the sampling disc chamber 206 to the slidable lid 210 is adapted such that the slidable lid does not come into contact with the adsorbent layer of a sampling disc 222 placed at the bottom of the desorption vessel 200, in order to avoid damage to or influence on the adsorbent and its collected substances.

An inlet port 214 comprising an inlet coupling 215 with a reduction union is arranged in fluid contact with the interior chamber 205 of the desorption vessel 200, preferably entering the larger volume chamber 208 for example through a passage in the top lid or in the wall of the main casing 201, preferably above the guiding grooves 212. A tube 216 is connected to the inlet coupling in order to supply an inert gas 218 such as nitrogen gas.

An outlet port 220 comprising an outlet port coupling 221 with a reduction union is arranged in fluid contact with the interior chamber 205 of the desorption vessel 200 as shown in FIG. 2B, preferably exiting from the larger volume chamber 208 for example through a passage in the wall of the main casing 201, preferably above the guiding grooves 212. As shown in FIG. 2C, the outlet port coupling 221 comprises a nut 224, a septum 226 and a reduction union 228. The purpose of the outlet port coupling 221 is on one hand to enable flushing the interior atmosphere via the outlet port when nut and septum are removed, and on the other hand to enable insertion of a needle through the septum when the nut and septum are tightened to close the outlet port in order to extract desorbed substances or analytes from the interior of the desorption vessel while keeping the interior atmosphere intact.

In exemplifying embodiments, the desorption vessel 200 is a box e.g. made of steel that has the interior measures of about 32 millimeters width, about 42 millimeters length and about 20 millimeters height. Wall thickness may be about 2 millimeters or more to allow for threaded couplings (214, 220) fitted in inlet and outlet bores, respectively. The reduction unions may have a reduction from 1/16 to 1/4 inches diameter. The nut 224 closing the septum 226 is then designed to fit a thread of 1/4 inches diameter. The tightly fitting and sealing top lid 202 may have a height of about 5 millimeters. The slidable lid 210 may be made of sheet metal and have a thickness of about 1 millimeter. A desorption vessel 200, adapted to sampling discs comprising a disc member having a thickness of about 1 millimeter plus an additional layer of glue and adsorbent, would suitably have the smaller volume chamber 206 arranged with an interior height of about 2 millimeters. In other words, the position of the slidable lid 210 would preferably be about 2 millimeters from the interior bottom of the desorption vessel 200.

FIG. 3 illustrates schematically a first method embodiment for extracting by desorption selected analytes from a collected sample of substances with a sample preparation apparatus according to the embodiment of FIG. 2. Different phases are illustrated and marked in FIG. 3.

In Phase 1 in FIG. 3, a sampling disc 222 that has been exposed to the exhalation of a test person is placed on the bottom of the desorption vessel 200 and the desorption vessel is closed by the schematically shown top lid 202. The inlet coupling 214 is connected to a supply of inert gas 218, e.g. nitrogen N2, possibly via a flow meter (not shown) and a pressure reduction valve (not shown) in order to fill the atmosphere of the interior chamber 205. Initially, as shown in Phase 1 of FIG. 3, the slidable lid 210 is extracted to its maximum, exposing the whole sampling disc 222 to the interior atmosphere and the outlet port 220 is kept open.

The gas supply is turned on to allow a flow of inert gas via the inlet coupling 214 into the interior chamber of the desorption vessel 200, and the interior atmosphere is flushed for a selected time period in room temperature. The time period may for example be in the range of 5 to 10 minutes. In exemplifying embodiments, the flow rate of the inert gas is in the range of 5 milliliters per minute, particularly in a desorption chamber with the dimensions and design as exemplified above.

In Phase 2 in FIG. 3, the outlet port 220 is closed and the inert gas flow is turned off. The desorption vessel 200, with its inert gas atmosphere in the interior chamber is then heated by a heat source 230 for a selected time period in order to induce release of substances from the adsorbent of the sampling disc. The slidable lid 210 is extracted and during heating the sampling disc is fully exposed to the interior atmosphere.

In embodiments, the heat source 230 is for example a hot plate or a heating block. The heat source may be a combined hot plate and magnetic stirrer, and in such an embodiment the desorption vessel 200 would be held firm and steady on the hot plate. As mentioned, the sampling disc lies on the bottom of the desorption vessel, which in its turn is in direct contact with the hot plate and the thermal transmission to the sampling disc 222 is efficient.

The heat source is heated or controlled to convey a heat adapted to fit the adsorbent on the sampling disc currently in desorption treatment. So, for example, for the adsorbents Tenax TA and Carbopak X the heat would be about 280 degrees Celcius and for the adsorbents Poropak Q or a mixture comprising Poropak Q the heat would be 250 degrees Celsius.

The desorption box with sampling disc is heated for a period in the range of about 5-10 minutes and substances that have been adsorbed on the sampling disc 222 are released during this procedure. Thereafter the slidable lid 210 is fully inserted and the sampling disc 222 is closed into the smaller volume chamber 206 close to the bottom of the desorption vessel 200 and is thus isolated from the atmosphere in the upper larger volume chamber 208 which now comprises desorbed substances to be analyzed. The heat is turned off and the heat source is taken away from the desorption vessel 200, or vice versa.

Phase 3A and 3B: In alternative embodiments Phase 3A and 3B illustrated in FIG. 3, desorbed substances or analytes are enriched and extracted from the upper larger volume chamber 208 of the desorption vessel 200 in preparation for separation and measuring substances. As shown in Phase 3A and Phase 3B of FIG. 3, the slidable lid is fully inserted into the desorption vessel. The purpose of the slidable lid 210 is to block the contact between the atmosphere in the larger volume chamber 208 of the desorption vessel and the sampling disc 222 when high temperature desorption of substances adsorbed on the sampling disc 222 has been carried out. Without this isolation of the sampling disc 222, the released substances would be re-adsorbed by the adsorbents of the sampling disc during the cooling of the desorption vessel. The volume in the lower sampling disc chamber 206 should be as small as possible and thus house as little as possible of released substances since this chamber is not available for analysis. By dividing the interior chamber 205 in this manner, the atmosphere in the upper larger volume chamber 208 is freely available for enrichment, for example in accordance with embodiments shown in Phase 3A and Phase 3B parts of FIG. 3, and there is therefore no need to move the atmosphere volume with analytes to a different container.

In Phase 3A, a first embodiment of enrichment and extraction of desorbed substance or analytes by means of solid phase microextraction is illustrated. Solid phase microextraction, in short also called SPME, is used to enrich and extract substances from the desorption vessel 200. In this phase, the slidable lid 210 is kept closed and the inert gas flow is kept turned off. A needle 231 with SPME fiber 232 is inserted through the septum 226 (cf. FIG. 2) of the outlet port coupling 221. The needle 231 with SPME fiber 232 is held by an SPME holder 234. For the SPME fiber 232 embodiments comprises for example CAR/PDMS fiber or DVB/CAR/PDMS fiber.

The needle with the SPME fiber is inserted and positioned such that the SPME fiber 232 is exposed to the atmosphere in the larger volume desorption chamber 208 of the desorption vessel. The SPME fiber is exposed to the atmosphere for a period of for example about 20-30 minutes until the desorption vessel has cooled to room temperature. During this period the fiber is enriched with substances or analytes from the atmosphere in the desorption vessel. The SPME fiber 232 with a sample of captured substances or analytes is then extracted with the needle 231 and SPME holder 234 the from the desorption vessel through the septum 226 of the outlet coupling 221.

The sample of analytes captured by the SPME fiber 232 is then ready for measuring by means of for example Gas chromatography-vacuum ultraviolet spectroscopy GC-VUV, mass spectrometry MS, flame ionization detection FID or some other suitable detection method and apparatus.

In Phase 3B, a second embodiment of enrichment and extraction of desorbed substances or analytes from the desorption vessel 200 by means of a needle trap device NTD 235 is illustrated. The needle trap device NTD 235 comprises an NTD needle 238 provided with an adsorbent in its lumen. The NTD needle 238 is coupled to a sampling pump 240 adapted for low fluid flow rates. In a preferred embodiment the NTD needle 238 is provided with an adsorbent in its lumen and in another embodiment the needle trap device NTD 235 comprises an NTD adsorbent chamber 236, where analytes are trapped and enriched.

In this embodiment, the enrichment is carried out when the desorption vessel has cooled. As shown in FIG. 3 Phase 3B, an NTD needle 238 is inserted into the desorption vessel 200 through the septum 226 (cf. FIG. 2) of the outlet port coupling 221. The sampling pump 240 is controlled to suck a flow through the NTD needle at a rate in the range of 3 milliliters per minute. In order to avoid negative pressure or even vacuum in the desorption vessel 200 an inert gas supply, for example nitrogen gas, is turned on and entered via the inlet port 214. The atmosphere in the larger volume chamber 208 is sucked through the NTD needle 238 and analytes are trapped and enriched in the adsorbent provided needle or, when present, in an NTD sorbent chamber 236.

The sample of analytes captured by means of the NTD device is then ready for measuring by means of for example Gas chromatography-vacuum ultraviolet spectroscopy GC-VUV, mass spectrometry MS, flame ionization detection FID or some other suitable detection method and apparatus.

Second Embodiment of Desorption Vessel and Desorption Method

Figure 4:
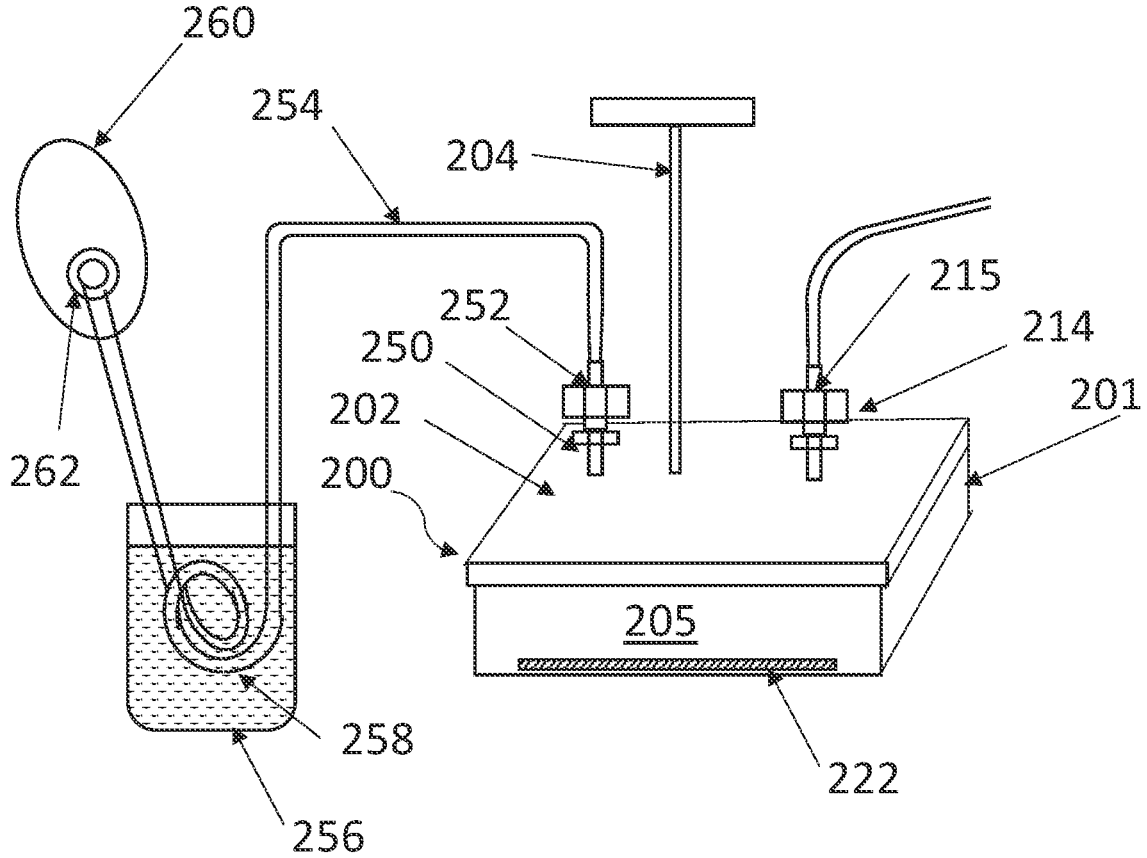
FIG. 4 shows another exemplifying embodiment of a sample preparation apparatus configured for extracting selected analytes from a collected sample of substances.

FIG. 4 shows a second exemplifying embodiment of a sample preparation apparatus configured for extracting selected analytes from a collected sample of substances. The structure is similar to the above described first embodiment and the same reference numbers are used for corresponding details that are similar in the two embodiments.

The second embodiment of the sample preparation apparatus comprises a desorption vessel 200 with a main casing 201, a tightly fitting and sealing top lid 202 and a handle 204 devised for lifting the lid 202 or the whole desorption vessel 200. The shape may for example be like a quadrangular box, made for example in steel or other suitable metal or metal alloy, and for example with interior dimensions in the range of 32 millimeters width, 42 millimeters length and 5 millimeters height. The wall thickness may be in the range of 1 millimeter thick if inlet and outlet ducts are welded connected to bores, or the wall thickness may be in the range of 2 millimeters to allow for threaded bores when that is preferred. The tightly fitting lid may have edges in the range of 2 millimeters high. The interior of the desorption vessel has a desorption chamber 205 and a sampling disc 222 is placed at the bottom of the desorption vessel. The volume of the desorption chamber should be as small as possible in order to keep the concentration of desorbed substances as high as possible and thereby also rendering the sensitivity of the analysis as high as possible.

In one variant embodiment, inlet and outlet ducts in the form of steel capillaries are welded to inlet and outlet bores in the lid. The capillaries may for example be in the range of 10 centimeters long, with 1.5 millimeters outer diameter and 0.5 millimeters inner diameter. In another variant embodiment, and as shown in the FIG. 4, the inlet and outlet ducts may be devised with threaded couplings and reduction units as described in connection with the first embodiment above.

Thus, an inlet port 214 comprising an inlet connection 215 or a capillary that is connected to a source of inert gas, such as nitrogen gas, via a flow meter and a reduction valve (not shown in FIG. 4).

An outlet port 250 comprising an outlet connection 252 or a capillary that is devised to lead substances in a desorption gas from the interior of the desorption chamber 200 via a tube 254 to a vessel 260 for collecting the desorbed substances.

In one variant embodiment, an outlet capillary is at the outlet end provided with a syringe needle (not shown). The syringe needle may be used to enter the outlet of desorption gas into a collection vessel 260 in the form of a bag in plastic or aluminum via a septum 262. The desorbed substances are transported in a desorption gas from the desorption vessel by means of pressurized inert gas entered via the inlet port 214.

As an alternative to a bag, a syringe (not shown) with a glass piston may be used as a collection vessel for the desorbed substances. Such a syringe may be calibrated with a volume for housing for example 20 or 50 milliliters of fluid. When the syringe is filled with gas the piston in the syringe will be moved by the gas pressure and the volume of the gas transferred from the desorption vessel 200 to the syringe may be read out from the calibration markings on the syringe.

A check valve may be comprised for example in the tube 254, in the collection vessel 260 or in the septum 262 in order to prevent outflow of collected desorption gas with desorbed substances from the collection vessel 260.

An embodiment comprises a moisture trap devised to capture any water that may be present in the desorption gas or in the inert gas. The moisture trap comprises a loop or a coil 258 of the tube 254 immersed in a cooling container 256. When the desorption gas is led past the cooled coil 258 of the tube 254, the water is condensed and frozen whereas other volatile substances continue to flow to the collection vessel 260. The cooling container may for example be filled with glycol having a temperature in the range of −20 degrees Celsius.

Figure 5:
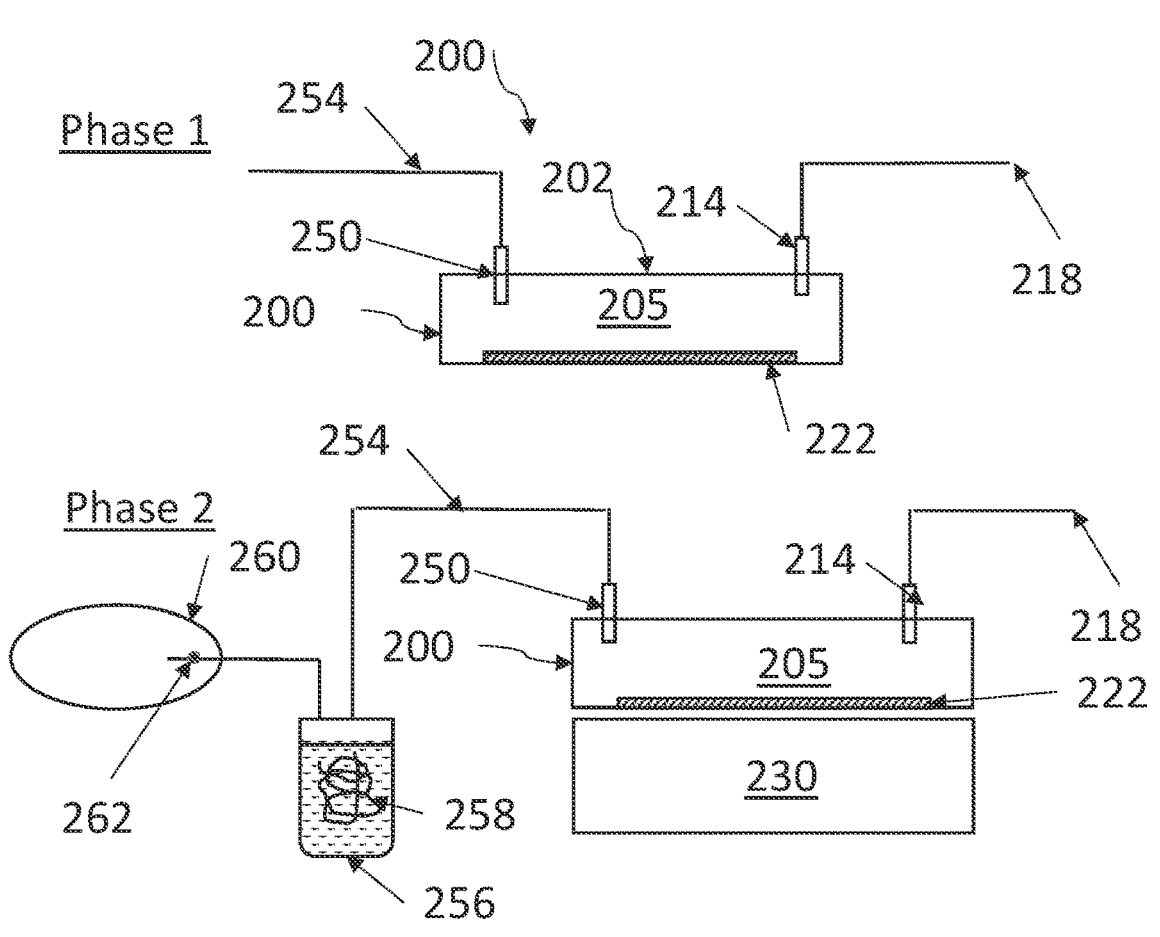
FIG. 5 illustrates schematically a second method for extracting selected analytes from a collected sample of substances with a sample preparation apparatus according to for example the embodiment of FIG. 4.
Figure 5:
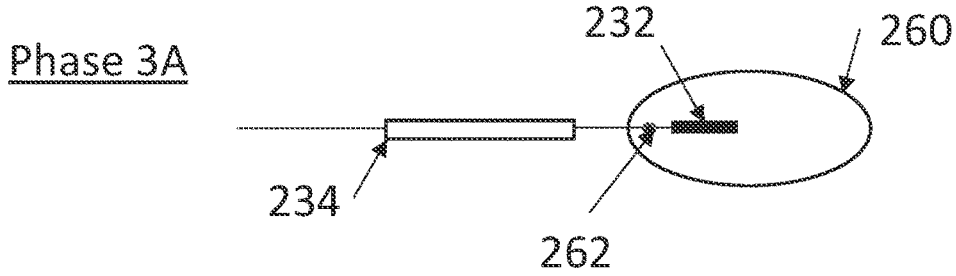
Figure 5:
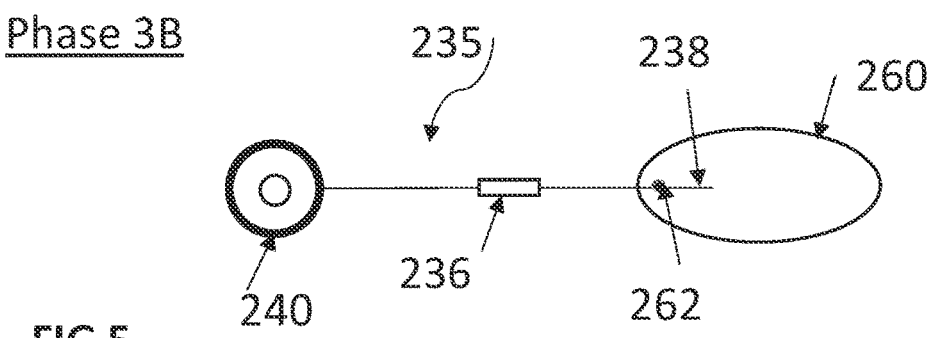

FIG. 5 illustrates schematically a second method embodiment for extracting selected analytes from a collected sample of substances with a sample preparation apparatus according to the embodiment of FIG. 4. Different phases are illustrated and marked in FIG. 5. This second method embodiment is particularly useful when the hydrophobic adsorbent, despite being hydrophobic, after all captures or has captured a certain amount of water. In such cases, the water will be released in the desorption process and may disturb the subsequent analysis with for example GC-VUV analysis methods.

In Phase 1 as illustrated in FIG. 5, a sampling disc 222, that has been exposed to the exhalation of a test person and taken off a headset of a sampling apparatus, is placed on the bottom of the desorption vessel 200. The desorption vessel 200 is closed by the top lid 202, schematically shown in FIG. 5.

A supply of inert gas 218 is connected to the inlet coupling 214. The desorption vessel is flushed with inert gas, as mentioned e.g. nitrogen N2, for a selected time period in the range of 5 to 10 minutes at room temperature. The flushing inert gas is allowed to escape from the desorption vessel via outlet port 250 and the tube 254. Thereafter the inert gas flow is turned off and preferably the outlet is closed. The flow rate of the inert gas in when flushing may for example be in the range of 5 milliliters per minute, for a desorption chamber with the dimensions and design as exemplified above.

In Phase 2 as illustrated in FIG. 5, the outlet port 250 and tube 254 is connected to a loop or coil 258 immersed in a cooling container 256 and further led to a collecting vessel 260 entered via a septum 262. The desorption vessel is heated by a heat source 230 with the temperatures for different specific adsorbents as described above.

The supply of inert gas is turned on with a flow rate in the range of 3 milliliters per minute and the desorption gas from the desorption vessel is allowed to flow past the coil 258 in the cooling container 256 and into the collecting vessel 260. The temperature of the cooling container is for example in the range of −20 degrees Celsius.

Desorption gas with desorbed substances to a volume of about 20-30 milliliters is collected in the collection vessel and then the desorption is interrupted by removing the heat and turning off the flow of inert gas.

In order to assess whether there is presence of water disturbing the analysis tests without condensation of water are comprised in variant embodiments. In cases of samples void of disturbance due to water content in the sample disc 222, the desorption gas may be led directly to the collection vessel 260 without passing the cooling container 256.

With this embodiment method the sampling disc is conditioned during the adsorption process and the sampling disc may be ready for use in a subsequent sampling, although a separate condition procedure may be present in preferred embodiments.

Phase 3A and 3B in FIG. 5 show alternative embodiments for enrichment and extraction of desorbed substances from the collection vessel 260.

Phase 3A in FIG. 5 illustrates a first embodiment of enrichment and extraction of desorbed substance or analytes by means of solid phase microextraction. Similar to the first method embodiment, solid phase microextraction, in short also called SPME, is used to enrich and extract substances from the collecting vessel 260. A needle 231 with SPME fiber 232 is inserted through the septum 262 of the collection vessel. The needle 231 with SPME fiber 232 may be held by an SPME holder 234. For the SPME fiber 232 embodiments comprises for example CAR/PDMS fiber or DVB/CAR/PDMS fiber.

The needle with the SPME fiber is inserted into the collection vessel 260 and positioned such that the SPME fiber 232 is exposed to the atmosphere in collection vessel 260. The SPME fiber is exposed to the atmosphere for a period of for example about 20-30 minutes until the gas in the collecting vessel 260 has cooled to room temperature.

During this period the fiber is enriched with substances or analytes from the atmosphere in the desorption vessel. The SPME fiber 232 with a sample of captured substances or analytes is then extracted with the needle 231 and SPME holder 234 the from the collection vessel 260 through the septum 262.

The sample of analytes captured by the SPME fiber 232 is then ready for measuring by means of for example Gas chromatography-vacuum ultraviolet spectroscopy GC-VUV, mass spectrometry MS, flame ionization detection FID or some other suitable detection method and apparatus.

Phase 3B, in FIG. 5 illustrates a second embodiment of enrichment and extraction of desorbed substances or analytes from the collection vessel 260 by means of a needle trap device NTD 235. Again similar to the first method embodiment, the needle trap device NTD 235 comprises an NTD needle 238 provided with adsorbent in its lumen or an NTD adsorbent chamber 236. The NTD needle 238 is coupled to a sampling pump 240 adapted for low fluid flow rates.

In this embodiment, the enrichment is carried out when the desorption gas in the collecting vessel 260 has cooled, for example to room temperature. As shown in FIG. 5 Phase 3B, an NTD needle 238 is inserted into the collection vessel 260 through the septum 262.

The sampling pump 240 is controlled to suck a flow through the NTD needle at a rate in the range of 3 milliliters per minute as long as there is desorption gas in the collecting vessel 260. The atmosphere of desorption gas in the collecting vessel 260 is sucked through the NTD needle 238 where analytes are trapped and enriched in the adsorbent in the needle lumen or, as in variant embodiments, in an NTD adsorbent chamber 236.

As in the first method embodiment, the sample of analytes captured by means of the NTD device is then ready for measuring by means of for example Gas chromatography-vacuum ultraviolet spectroscopy GC-VUV, mass spectrometry MS, flame ionization detection FID or some other suitable detection method and apparatus.

Analysis

Analysis of the substances that have been collected from a test person on a sampling disc is carried out on the collection of substances enriched by means of SPME or NTD with different methods as exemplified above.

When using a GC-VUV equipment (GC-VUV=Gas chromatography-vacuum ultraviolet spectroscopy) the SPME or the NTD sample holder is inserted into an injector of the Gas Chromatography (GC injector) for desorption. The adsorbed substances are released in the GC injector, are then separated on a GC capillary column and detected by means of the VUV detector.

In embodiments of an analysis method, a nitrogen flow is adjusted to 0.5 milliliters per minute and the temperature on the GC column devised and programmed as follows:

1. A starting temperature in the range of 40 degrees Celsius for a time period of about 1 minute;
2. Then a ramp of temperature raising by 8 degrees Celsius per minute to about 200 degrees Celsius; and thereafter
3. A ramp of temperature raising by 10 degrees Celsius per minute to a resulting temperature of 250 degrees Celsius.

The wavelength range for the VUV detector is for example in the range of 125-240 nanometers.

The wavelength range for the VUV detector may be adjusted in view of evaluation of obtained results such that the substances that are relevant for selected analyses are specifically detected. Substances are identified by means of the VUV spectrum library or by means of measurements of selected reference substances that are relevant.

Semiquantitative assessments, i.e. assessments of relative concentrations of separate detected substances in a mixture, is conducted by integrating the area below detected chromatographic peaks that are detected in the mixture and by relating each individual peak to the total amount. Quantitative assessment is carried out by means of calibrating the GC system with known amounts of reference substances for each separate target substance.

Comparisons between measurements conducted by means of SPME and NTD are carried out and what appears to be the most appropriate analysis method is selected for further analyses. Also comparative analyses carried out by means of GC-MS (GC-MS=Gas Chromatography-mass spectrometry) may be useful and relevant, since GC-MS often has a higher sensitivity than GC-VUV.

Evaluation

In evaluation of the analysis results, for example in order to detect markers for cancer disease, there is an assessment whether there is a difference in occurrence or concentration of substances in the exhalation breath from cancer patients compared to the content in the exhalation breath from healthy test persons. Such substances that show a significant difference are selected as cancer markers. In cases where no significant difference between populations of healthy persons and cancer patients is detected, other methods such as chemometric methods are used in evaluation in order to distinguish healthy test persons from cancer patients.

The invention claimed is:

1. A system for breath analysis, comprising:
a. a breath sampling apparatus configured for collecting, from an exhalation breath of a test subject, a sample of substances on a sampling disc devised with an adsorbent, wherein the breath sampling apparatus comprises a headset comprising a holder for said sampling disc and the holder being arranged on the headset such that the holder is adjustable to be placed in proximity of exhalation openings of a test person carrying the headset; and
b. a sample preparation apparatus configured for extracting, by thermal desorption, selected analytes from the sample of substances collected on said sampling disc, wherein the sample preparation apparatus comprises a desorption vessel comprising a main casing and a top lid, the desorption vessel having an interior adapted to accommodate said sampling disc and further being provided with an inlet port for inlet of an inert gas and an outlet port for outlet of desorbed substances from the interior of the desorption vessel, and wherein the desorption vessel comprises a slidable lid adapted to selectively partition the interior of the desorption vessel into two chambers when fully inserted, such that a first chamber is formed in the desorption vessel to be able to accommodate the sampling disc, and a second chamber; such that said second chamber is fully exposed to the sampling disc placed in the first chamber when the slidable lid is extracted and such that said second chamber is shielded from the sampling disc placed in the first chamber when the slidable lid is fully inserted.

2. The system of claim 1, wherein the breath sampling apparatus is devised such that the sampling disc is attachable by a magnet or other mechanical arrangement.

3. The system of claim 1, wherein the sampling disc comprises a disc member provided with an adsorbent attached to a surface area of the disc member.

4. The system of claim 3, wherein the sampling disc comprises an adsorbent powder glued to the disc member.

5. The system of claim 1, wherein the sample preparation apparatus comprises a moisture trap adapted to condense and possibly freeze any water content present with the desorbed substances extracted from the desorption vessel.

6. The system for breath analysis of claim 1, further comprising a breath sample container for intermediate storage of the sampling disc with the sample of substances collected from the exhalation breath of a test subject.

7. The system for breath analysis of claim 1, further comprising an apparatus for detecting and measuring analytes in a collection of substances extracted from the sampling disc.

8. A method of breath analysis comprising:
a. placing a sampling disc devised with an adsorbent in proximity of exhalation openings of a test person by a breath sampling apparatus configured for collecting, from an exhalation breath of a test subject, a sample of substances on said sampling disc devised with an adsorbent, wherein the breath sampling apparatus comprises a headset comprising a holder for said sampling disc and the holder being arranged on the headset such that the holder is adjustable to be placed in said proximity of the exhalation openings of a test person carrying the headset;
b. receiving the exhalation breath on the sampling disc for a predetermined period of time;
c. collecting the sample of substances from the exhalation breath by adsorption on the sampling disc, wherein the adsorbed amount and composition of substances corresponds to an average amount and composition of substances exhaled during a length of time;
d. placing the sampling disc with the collected substances in a desorption vessel, wherein the desorption vessel comprises a main casing and a top lid, the desorption vessel comprising an interior adapted to accommodate said sampling disc and further being provided with an inlet port for inlet of an inert gas and an outlet port for outlet of desorbed substances from the interior of the desorption vessel, and wherein the desorption vessel comprises a slidable lid adapted to selectively partition the interior of the desorption vessel into two chambers when fully inserted, such that a first chamber, is formed in the desorption vessel to be able to accommodate the sampling disc, and a second chamber, is fully exposed to the sampling disc placed in the first chamber when the slidable lid is extracted and said second chamber is shielded from the sampling disc placed in the first chamber when the slidable lid is fully inserted;

e. releasing by thermal desorption the collected substances from the sampling disc in the desorption vessel by heating in an inert atmosphere;

f. preparing a sample by adsorption of selected analytes among the sample of substances; and g. analyzing said selected analytes.

9. The method of claim 8, further comprising:

capturing any water content present among the collected substances by condensation.

10. The method of claim 8, wherein preparing the sample further comprises adsorption of said selected analytes by Solid Phase Microextraction (SPME).

11. The method of claim 8, wherein preparing the sample further comprises adsorption of said selected analytes by a Needle Trap Device (NTD).

12. The method of claim 8, wherein analyzing said selected analytes comprises analysis by a selection of: Gas chromatography-vacuum ultraviolet spectroscopy GC-VUV, mass spectrometry MS, or flame ionization detection FID.

13. A breath sample preparation apparatus comprising a desorption vessel comprising a main casing and a top lid, the desorption vessel having an interior adapted to accommodate a sampling disc devised with an adsorbent and further being provided with an inlet port for inlet of an inert gas and an outlet port for outlet of desorbed substances from the interior of the desorption vessel; and wherein the desorption vessel comprises a slidable lid adapted to selectively partition the interior of the desorption vessel into two chambers when fully inserted, such that a first chamber is formed in the desorption vessel to be able to accommodate the sampling disc, and a second chamber is fully exposed to the sampling disc placed in the first chamber when the slidable lid is extracted and said second chamber is unaffected by the sampling disc placed in the first chamber when the slidable lid is fully inserted.

14. The breath sample preparation apparatus of claim 13, wherein the sample preparation apparatus comprises a moisture trap adapted to condense and possibly freeze any water content present with the desorbed substances extracted from the desorption vessel.

15. The breath sample apparatus of claim 13, further comprising a breath sample container for intermediate storage of the sampling disc with a sample of substances collected from an exhalation breath of a test subject.

16. The system of claim 1, wherein the slidable lid is adapted to selectively partition the interior of the desorption vessel into the two chambers when fully inserted such that said second chamber is unaffected by the sampling disc placed in the first chamber when the slidable lid is fully inserted.

17. The method of claim 8, wherein the slidable lid is adapted to selectively partition the interior of the desorption vessel into the two chambers when fully inserted such that said second chamber is unaffected by the sampling disc placed in the first chamber when the slidable lid is fully inserted.

* * * * *